US012805820B2

(12) United States Patent
Ono et al.

(10) Patent No.: US 12,805,820 B2
(45) Date of Patent: Nov. 24, 2026

(54) MOBILE RADIOGRAPHIC IMAGING SYSTEM AND METHOD FOR RESTRICTING MOBILE RADIOGRAPHIC IMAGING SYSTEM

(71) Applicant: Konica Minolta, Inc., Tokyo (JP)

(72) Inventors: Kojiro Ono, Chiba (JP); Yousuke Suzuki, Tokyo (JP); Takanori Kakigi, Tokyo (JP); Takeshi Murayama, Tokyo (JP)

(73) Assignee: Konita Minolta, Inc., Tokyo (JP)

( * ) Notice: Subject to any disclaimer, the term of this patent is extended or adjusted under 35 U.S.C. 154(b) by 202 days.

(21) Appl. No.: 18/925,817

(22) Filed: Oct. 24, 2024

(65) Prior Publication Data

US 2025/0134479 A1 May 1, 2025

(30) Foreign Application Priority Data

Oct. 26, 2023 (JP) ................................ 2023-183880
Aug. 27, 2024 (JP) ................................ 2024-145401

(51) Int. Cl.
*A61B 6/00* (2024.01)
*A61B 6/10* (2006.01)
(Continued)

(52) U.S. Cl.
CPC ............ *A61B 6/4405* (2013.01); *A61B 6/105* (2013.01); *A61B 6/107* (2013.01); *A61B 6/46* (2013.01);
(Continued)

(58) Field of Classification Search
CPC ....... A61B 6/487; A61B 6/4405; A61B 6/107; A61B 6/46; A61B 6/54; A61B 6/105;
(Continued)

(56) References Cited

U.S. PATENT DOCUMENTS

2001/0036245 A1* 11/2001 Kienzle, III ....... A61B 17/1703 378/4
2007/0029492 A1* 2/2007 Abe ........................ G01T 7/005 250/370.09

(Continued)

FOREIGN PATENT DOCUMENTS

JP 2015100462 A 6/2015
JP 2021053168 A 4/2021

(Continued)

OTHER PUBLICATIONS

Japanese Office Action dated Sep. 30, 2025 issued for Japanese patent application No. 2024-145401 and its English machine translation.

*Primary Examiner* — Irakli Kiknadze
(74) *Attorney, Agent, or Firm* — RANKIN, HILL & CLARK LLP

(57) ABSTRACT

A mobile radiographic imaging system includes a radiation generation apparatus that emits radiation and can be set to a plurality of imaging modes including a first mode for performing fluoroscopic imaging and a second mode that is a general imaging mode and acquires a series of frame images by irradiating a subject with the radiation, and a hardware processor that restricts the use of the first mode outside a management area.

14 Claims, 6 Drawing Sheets

(51) Int. Cl.
*A61B 6/46* (2024.01)
*G16H 10/60* (2018.01)
*G16H 40/63* (2018.01)

(52) U.S. Cl.
CPC ................ *A61B 6/487* (2013.01); *A61B 6/54* (2013.01); *G16H 10/60* (2018.01); *G16H 40/63* (2018.01)

(58) Field of Classification Search
CPC ......... A61B 6/542; A61B 6/544; A61B 6/545; A61B 34/10; A61B 34/30; A61B 34/20; A61B 2034/2065; A61B 2034/2055; A61B 2034/107; A61B 2090/376; A61B 2034/108; A61B 2090/365; A61B 6/0487; A61B 6/4014; A61B 6/4441; A61B 6/4476; A61B 6/463; A61B 6/467; A61B 2560/0295; A61B 17/70; A61B 17/7002; A61B 17/7019; A61B 17/7074; A61B 17/8863; A61B 34/25; A61B 2034/104; A61B 2034/105; A61B 2034/252; A61B 2034/254; A61B 2034/256; A61B 2090/364; A61B 6/025; A61B 6/032; A61B 6/4429; A61B 6/4452; A61B 6/03; A61B 6/461; A61B 6/482; A61B 6/481; A61B 6/504; A61B 6/5235; A61B 34/73; A61B 34/72; A61B 2034/731; A61B 2034/732; A61B 2090/3764; A61B 1/00149; A61B 1/2676; A61B 34/70; A61B 6/4266; A61B 6/4435; A61B 6/4482; A61B 6/56; A61B 6/563; A61B 6/06; A61B 6/42; A61B 6/4233; A61B 6/462; A61B 6/547; A61B 6/464; G16H 10/60; G16H 40/63; G16H 40/20; G16H 40/40; G16H 40/67; G16H 50/50; G16H 20/40; G16H 30/40; G16H 10/00; G06T 7/0012; G06T 2200/24; G06T 2207/10121; G06T 2207/20081; G06T 2207/20084; G06T 2207/30168; G06T 19/006; G06T 17/00; G06T 19/00; G06T 2210/41; G06F 3/011; G06F 3/167; G06F 3/013; G06F 3/012; G06F 3/017; G06F 3/0484; G06F 3/0488; G06N 20/00; G06N 3/045; G06N 3/0464; G06N 3/08; G06N 3/09; A61M 25/0127; H05G 1/32
USPC .................................................... 378/62, 198
See application file for complete search history.

(56) References Cited

U.S. PATENT DOCUMENTS

| | | | | |
|---|---|---|---|---|
| 2015/0036803 | A1* | 2/2015 | Kuroki | A61B 6/463 378/98.5 |
| 2015/0100290 | A1* | 4/2015 | Falt | G16H 50/50 703/2 |
| 2021/0137477 | A1* | 5/2021 | O'Dea | A61B 6/06 |
| 2023/0040643 | A1* | 2/2023 | Ruff | A61B 6/08 |
| 2024/0045404 | A1* | 2/2024 | Sinha | G05B 19/4155 |
| 2025/0302535 | A1* | 10/2025 | Schmidt-Richberg | A61B 34/20 |

FOREIGN PATENT DOCUMENTS

| | | | |
|---|---|---|---|
| JP | 2022011259 | A | 1/2022 |
| WO | 2021085245 | A1 | 5/2021 |

* cited by examiner

MOBILE RADIOGRAPHIC IMAGING SYSTEM AND METHOD FOR RESTRICTING MOBILE RADIOGRAPHIC IMAGING SYSTEM

CROSS REFERENCE TO RELATED APPLICATIONS

The entire disclosures of Japanese Patent Application No. 2024-145401 filed on Aug. 27, 2024 and Japanese Patent Application No. 2023-183880 filed on Oct. 26, 2023 are incorporated herein by reference in their entirety.

BACKGROUND

Technological Field

The present disclosure relates to a mobile radiographic imaging system and a method for restricting the mobile radiographic imaging system.

Description of Related Art

A fluoroscopy apparatus that continuously emits pulsed radiation to perform fluoroscopic imaging of a subject has been proposed (e.g., Japanese Unexamined Patent Publication No. 2021-53168). Fluoroscopic imaging emits a larger dose of radiation than general imaging.

In a building such as a hospital that handles fluoroscopy apparatuses, a room serving as a management area (simply referred to as a “management area”) is installed. According to the Japanese law, the fluoroscopic apparatus must be used in a strictly management area as compared to a general imaging apparatus, and thus cannot be used in a general hospital room. Therefore, when fluoroscopic imaging is performed, the patient needs to move to an imaging room where the fluoroscopy apparatus can be used, and in the case of a patient who is difficult to move to the imaging room, such as a critically ill patient or an infected patient, the physical burden on the patient is large. In addition, when a severe patient or a patient with an infectious disease is moved, it is necessary to assist the movement or to construct an environment for a countermeasure against infection, which increases the physical burden and the time burden on healthcare professionals.

The above-described problem can be solved when a mobile dynamic imaging apparatus (for example, Japanese Unexamined Patent Publication No. 2022-11259) capable of capturing moving images even in a general hospital room is held in hospitals. However, it is a large financial burden for hospitals to hold a fluoroscopic apparatus and a mobile dynamic imaging apparatus, and it is difficult to hold both a fluoroscopic apparatus and a mobile dynamic imaging apparatus particularly for small-scale hospitals and clinics.

SUMMARY

An object of the present disclosure is to provide a mobile radiographic imaging system capable of reducing a burden on subjects or healthcare professionals.

The present inventors have considered that the above-described problem can be solved by providing a mobile radiographic imaging system having a plurality of imaging modes including an imaging mode in which fluoroscopic imaging is performed and a dynamic imaging mode which is a general imaging mode in which a series of images of a plurality of frames are acquired by irradiating a subject with radiation. However, since available places are different between fluoroscopic imaging and general imaging, it is necessary to perform imaging by an appropriate method according to the place. To solve a new problem that a patients and healthcare professionals may be unnecessarily exposed when fluoroscopic imaging is performed in an unusable place by mistake.

A mobile radiographic imaging system according to an embodiment of the present disclosure includes a radiation generation apparatus that emits radiation and can be set to a plurality of imaging modes including a first mode for performing fluoroscopic imaging and a second mode that is a general imaging mode in which a series of frame images is acquired by irradiating a subject with radiation, and a control device that restricts use of the first mode outside a management area.

A method for restricting a mobile radiographic imaging system according to an embodiment of the present disclosure restricts, in a mobile radiographic imaging system capable of setting a plurality of imaging modes including a first mode for performing fluoroscopic imaging and a second mode that is a general imaging mode in which a series of frame images is acquired by irradiating a subject with radiation, use of the first mode outside a management area.

Note that these generic or specific aspects may be implemented as a system, an apparatus, a method, an integrated circuit, a computer program, or a recording medium, or any selective combination of a system, an apparatus, a method, an integrated circuit, a computer program, and a recording medium.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

In the following, embodiments of the present disclosure will be described in detail with reference to the drawings as appropriate.

<1. Mobile Radiographic Imaging System>

First, a schematic configuration of a mobile radiographic imaging system according to an embodiment of the present disclosure will be described. The mobile radiographic imaging system includes at least a radiation generation apparatus. The mobile radiographic imaging system may be, for example, a medical cart 100. The medical cart 100 may have an automatic driving function.

Figure 1:
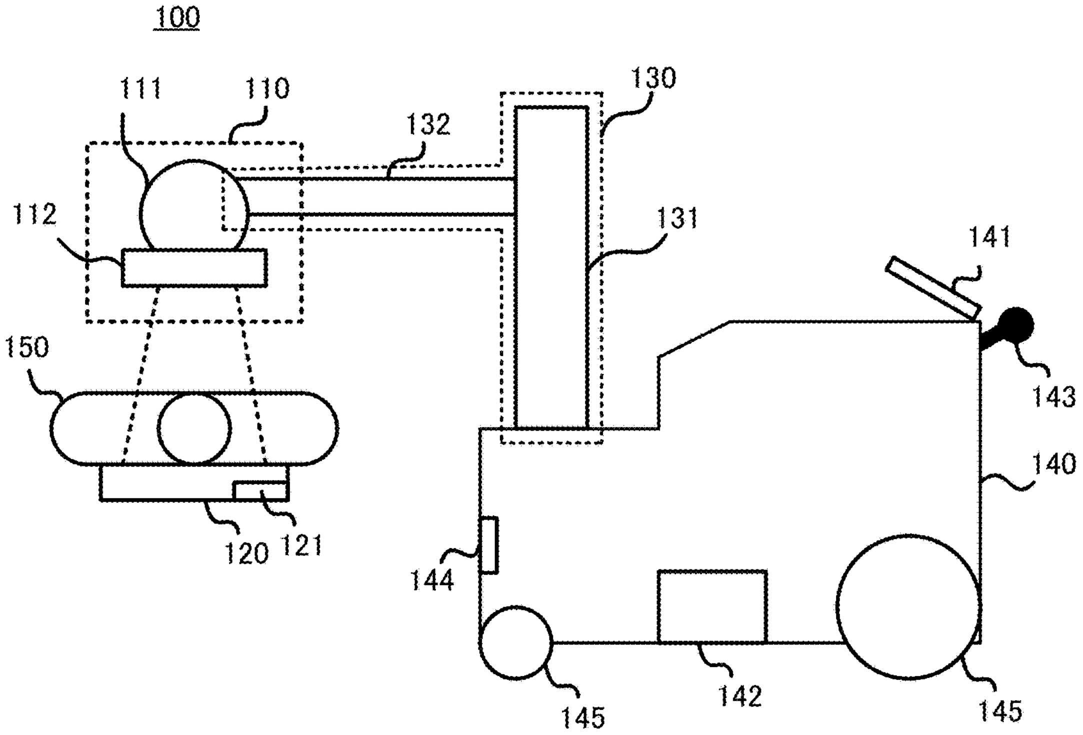
FIG. 1 is a diagram illustrating an example of a medical cart in use.

FIG. 1 is a diagram illustrating an example of a medical cart 100 in use.

Figure 2:
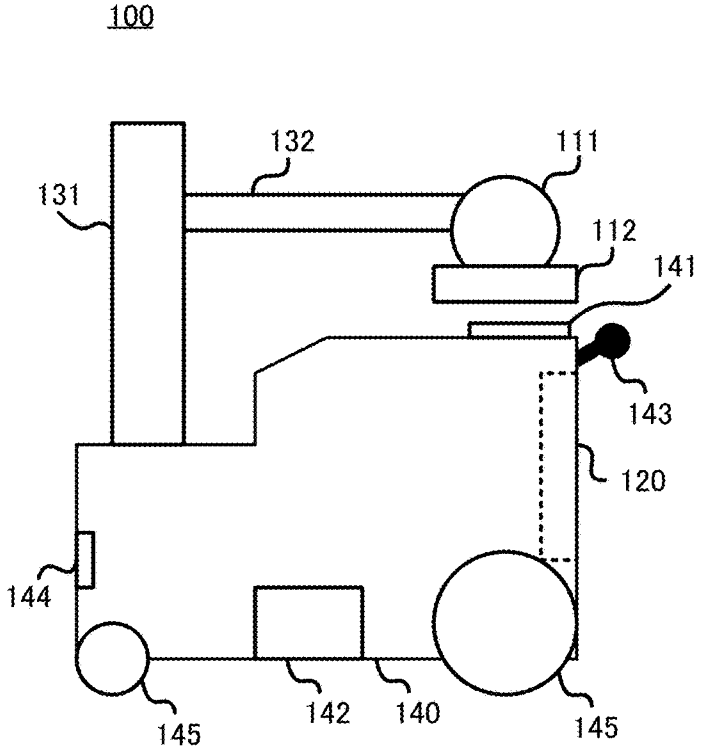
FIG. 2 is a diagram illustrating an example of the medical cart while moving or not in use.

FIG. 2 is a diagram illustrating an example of the medical cart 100 when the medical cart 100 is moved or not used.

The medical cart 100 includes a radiation generation apparatus 110, a radiation detection apparatus 120, an arm 130, and a main body 140. The medical cart 100 can be set to at least a fluoroscopy mode as a first mode or a dynamic imaging mode as a second mode as the imaging mode of the radiation generation apparatus 110. The medical cart 100 can be used as a fluoroscopy apparatus when the imaging mode is set to the fluoroscopy mode, and can be used as a dynamic imaging apparatus when the imaging mode is set to the dynamic imaging mode. The radiation generation apparatus 110 may have three or more imaging modes.

The medical cart 100 may be configured to communicate with a hospital information system (HIS), a radiology information system (RIS), an image analyzing apparatus, a picture archiving and communication system (PACS), another radiographic imaging apparatus, and the like, which are not illustrated.

[Radiation Generation Apparatus]

The radiation generation apparatus 110 is mounted on the medical cart 100 and includes a generator 111 and a collimator 112. The radiation generation apparatus 110 may be a radiation generating unit.

The generator 111 includes a tube. When a voltage is applied to the tube and a current flows, radiation is emitted from the tube. A pulsed voltage may be applied to the tube, and pulsed radiation, for example, X-rays may be emitted from the tube.

The maximum radiation dose that the generator 111 emits, that is, the allowed radiation dose is limited according to the imaging mode set in the medical cart 100. In the dynamic imaging mode, the radiation dose to be emitted is limited due to the limitation as a general imaging apparatus. In the fluoroscopic mode, since there is no limitation as a general imaging apparatus, a larger radiation dose can be emitted than in the dynamic imaging mode. In the fluoroscopy mode, the radiation dose does not have to be limited. The generator 111 emits radiation on the basis of the setting from the input section. The imaging conditions are, for example, conditions related to the subject 150 such as an imaging site, an imaging direction, and a physique, and conditions related to radiation emission such as a tube voltage, a tube current, an emission time, a current-time product (mAs value), a frame rate, an allowable number of frames, a pulse width, a pulse interval, a pulse cycle, and a pulse duty ratio.

In the dynamic imaging mode, the radiation generation apparatus 110 repeatedly emits radiation at a cycle multiple times per unit time (for example, 15 times per second) for a predetermined time (duration) while an emission instruction is issued. Here, the pulse period and the duration are set in advance by the input/output section 141. The pulse interval, the pulse width, and the duty ratio of the pulse may be set in advance by the input/output section 141. Although a configuration in which radiation pulses are emitted in the dynamic imaging mode according to this embodiment will be described as an example, a configuration in which radiation is continuously emitted may be employed. In the dynamic imaging mode, emission of radiation is limited due to limitations as a general imaging apparatus.

In the fluoroscopy mode, the radiation generation apparatus 110 repeats a radiation pulse at a cycle multiple times per unit time (e.g., six times, ten times, or fifteen times a second) while an emission instruction is given. Here, the pulse period is set in advance by the input/output section 141. In the fluoroscopy mode, no duration is set. That is, in the fluoroscopic mode, the emission of the radiation is not limited by the duration. Further, in the fluoroscopic mode, since there is no limitation as a general imaging apparatus, more radiation can be emitted than in the dynamic imaging mode. In the fluoroscopy mode, the radiation dose does not have to be limited. The pulse interval, the pulse width, and the duty ratio of the pulse may be set in advance by the input/output section 141. Note that a configuration in which a radiation pulse is emitted in the fluoroscopy mode in this embodiment will be described as an example, but a configuration in which radiation is continuously emitted may be employed.

The collimator 112 narrows an irradiation field of the emitted radiation. The collimator 112 may have a shielding means such as a filter. The shielding means may narrow a region to be irradiated with the emitted radiation. The shielding means may weaken the intensity of the emitted radiation.

[Radiation Detection Apparatus]

The radiation detection apparatus 120 includes a communicator 121. Although not illustrated, the imaging device further includes a sensor board, a scanning circuit, a readout circuit, and a controller. The radiation detection apparatus 120 may be a radiation detection unit.

The radiation detection apparatus 120 detects radiation emitted from the radiation generation apparatus 110 through the subject 150. The subject 150 is, for example, a human, an animal, or the like.

In the sensor substrate, pixels are arranged two-dimensionally (in a matrix). Each pixel includes a radiation detection element that generates an electric charge corresponding to the dose of radiation received through a subject and a switch element that accumulates and discharges the electric charge. The scanning circuit sets ON or OFF of each switch element. The readout circuit reads out the amount of charge emitted from each pixel as a signal value (intensity). The controller controls the entire radiation detection apparatus 120. The controller generates a radiation image from the plurality of signal values read by the reading circuit. The communicator 121 transmits the data of the radiographic image generated by the readout circuit, various signals, and the like to the outside. Further, the communicator 121 receives various types of information and various signals. The communicator 121 may perform wireless communication or may perform wired communication.

In each pixel of the radiation detection apparatus 120 configured in such a manner, when the radiation detection element receives radiation in a state in which the scanning circuit turns off the switch element, the radiation detection element generates electric charge corresponding to the dose of radiation and accumulates the electric charge. When the scanning circuit turns on the switch elements, the accumulated charges are released, and the readout circuit detects the amount of charges released from each pixel and generates a signal value indicating the amount of charges. The controller generates a radiographic image based on the signal value generated for each pixel. The generated individual radiographic images are one still image in the dynamic imaging. In the case of pulsed radiation, one static image is generated for each pulse.

The communicator 121 communicates with the communicator 144 of the main body 140 and transmits the generated radiographic image to the communicator 144 of the main body 140. The communicator 121 may transmit the still image to the main body 140 each time one still image is generated, or may collectively transmit a plurality of still images to the communicator 144 of the main body 140. The communicator 121 may communicate with another component other than the main body 140. The communication performed by the communicator 121 may be wireless communication or wired communication.

In a case where the radiation generation apparatus 110 performs pulse emission, timings at which a plurality of still images constituting a dynamic image are generated are synchronized with timings at which radiation is emitted from the radiation generation apparatus 110. On the other hand, in a case where the radiation generation apparatus 110 performs continuous emission, generation of a plurality of still images forming a dynamic image is performed at arbitrary timings during the time of continuous emission.

The radiation detection apparatus 120 may be stored in a storage provided in the main body 140 when the medical cart 100 is moved or not in use. When the radiation detection apparatus 120 is stored in the storage of the main body 140, the radiation detection apparatus 120 may be connected to the main body 140 in a wired manner, and charging of the radiation detection apparatus 120 from the main body 140 and communication with the main body 140 may be performed. When the radiation detection apparatus 120 is stored in the storage of the main body 140, software or firmware of the radiation detection apparatus 120 may be updated by communication with the main body 140. Charging of the radiation detection apparatus 120 and communication with the main body 140 may be performed wirelessly.

The radiation detection apparatus 120 may be wirelessly connected during use. The radiation detection apparatus 120 may be driven by an internal battery. Power may be supplied to the radiation detection apparatus 120 from the main body 140 in a wired or wireless manner.

The radiation detection apparatus 120 may be connected to the main body 140 in a wired manner when being moved or not being used, and may be connected to the main body 140 in a wireless manner when being used.

[Arm]

The arm 130 includes a vertical arm 131 and a horizontal arm 132. The vertical arm 131 supports the horizontal arm 132 so as to be pivotable, that is, rotatable with respect to the Z axis. Furthermore, the vertical arm 131 may movably support the horizontal arm 132. The horizontal arm 132 supports the radiation generation apparatus 110 so as to be rotatable, that is, rotatable with respect to the X-axis and the Y-axis. The radiation generation apparatus 110 can be oriented in any direction with respect to the main body 140 by the vertical arm 131 and the horizontal arm 132. The position and orientation of the arm may be determined by input from the input/output section 141. The vertical arm 131 and the horizontal arm 132 may be rotatable and movable by control from the main body 140 or may be rotatable and movable manually.

[Main Body]

The main body 140 includes an input/output section 141, a power supply section 142, a communicator 144, and wheels 145. The main body 140 may include a handle 143. Although not illustrated, the main body 140 may include a storage that stores the radiation detection apparatus 120. Communication between the communicator 144 of the main body 140 and the communicator 121 of the radiation detection apparatus 120 may be wireless communication or wired communication.

Although not illustrated, the main body portion 140 may have a fixer for locking the movement. By releasing the fixer, the main body 140 can be moved. For example, the fixer may be means for fixing the wheel 145, or may be means for fixing the medical cart 100 to a wire fixed to a wall forming the management area.

The input/output section 141 can have a variable inclination angle with respect to the main body 140. The input/output section 141 may be separable from the main body 140. When the input/output section 141 is separated from the main body 140, the input/output section 141 and the main body 140 are connected to each other in a wireless or wired manner.

The input/output section 141 includes an input means and an output means. The input/output section 141 may be divided into an input section and an output section. The input/output section 141 may include a touch panel, a keyboard, a mouse, a microphone, a camera, a display, a speaker, a display lamp, and the like. As the input/output section 141, input means such as an input by voice, an input by gesture, an input by line of sight, and an input by brain waves may be available. The input/output section 141 performs setting of the radiation generation apparatus 110. The input/output section 141 can input an operation for instructing the radiation generation apparatus 110 to perform emission. The input/output section 141 may configure the emission instruction switch with an emission button of a toggle button and output the emission instruction during a period from when the toggle button is pressed for the first time to when the toggle button is pressed for the second time, or may output the emission instruction during a period in which the emission button is continuously pressed.

In response to an operation of the input/output section 141, the generator 111 emits radiation of a dose set by the input/output section 141. The radiation is, for example, X-rays.

Various parameters emitted by the radiation generation apparatus 110 are input to the input section. Mode setting may be input to the input section. When the medical cart 100 is set to the dynamic imaging mode by the controller, the input section may be prohibited from inputting a setting that exceeds the radiation dose allowed in the dynamic imaging mode.

The output section provides a notification related to the setting of the mode. The output section may provide a notification prompting the user to change from the fluoroscopy mode to the dynamic imaging mode. The output section may provide a notification regarding the current mode of the medical cart 100. The output section may provide a notification that the setting from the fluoroscopy mode to the dynamic imaging mode has been performed. The output section may issue a warning. Note that the notification will be described in detail later.

The power supply section 142 supplies power to the entire main body 140. The power supply section 142 may charge the radiation detection apparatus 120. The power supply section 142 may be constituted by a rechargeable battery. The power supply section 142 may be charged by being connected to a commercial power supply or the like. The battery charger may have a function of detecting that charging has started. The power supply section 142 may be, for example, a nickel-metal hydride battery, a lithium-ion battery, a sodium battery, an all-solid-state battery, or a flywheel. The power supply section 142 may be constituted by a fuel cell or a nuclear battery. The fuel cell may be refillable with fuel.

The power supply section 142 may be connected to a commercial power supply or the like to perform charging when not in use, and may be disconnected from the commercial power supply to perform power supply by a battery when in use. The power supply section 142 may be replenished with fuel of the fuel cell when not in use.

The handle 143 is held by a person when the medical cart 100 is moved. A sensor built in the handle 143 may detect that it is held by a person. Upon detection of being held by a person, the sensor may provide a notification to the control circuit 330.

The communicator 144 communicates with the communicator 121 of the radiation detection apparatus 120. The communicator 144 transmits the setting and the instruction set by the input/output section 141 to the communicator 121 of the radiation detection apparatus 120. The communicator 144 outputs the radiographic image received from the communicator 121 of the radiation detection apparatus 120 to the input/output section 141.

The wheels 145 rotate when the medical cart 100 is moved. The wheel 145 may be rotated (driven) by electric power supplied from the power supply section 142, or may be rotated by a person pressing the medical cart 100 with the handle 143. The wheel 145 is fixed by a fixer (not illustrated).

[Functional Blocks]

Figure 3:
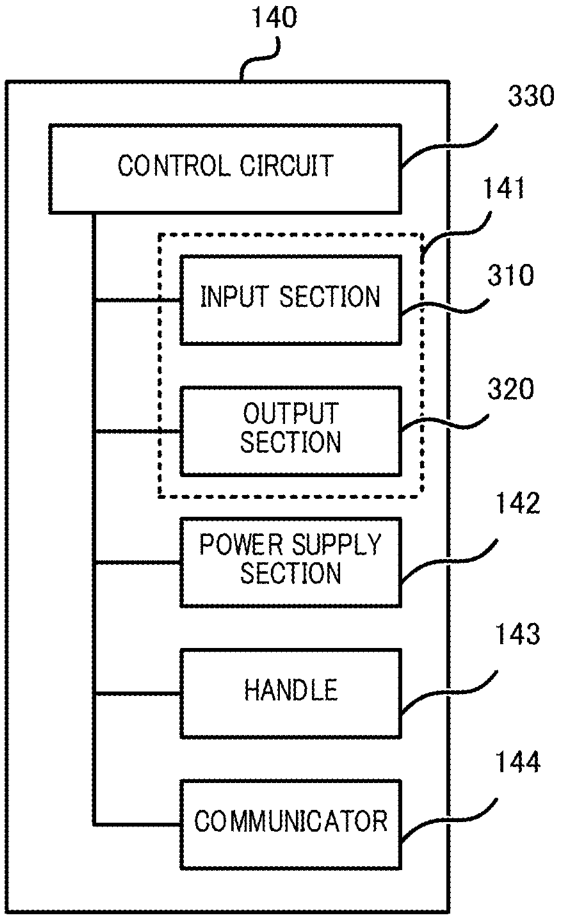
FIG. 3 is a diagram illustrating functional blocks of a main body.

FIG. 3 is a diagram illustrating functional blocks of the main body 140. The main body 140 includes an input section 310, an output section 320, a power supply section 142, a handle 143, a communicator 144, and a control circuit 330. The input section 310 and the output section 320 form an input/output section 141. The input section 310 and the output section 320 may be integrated.

The input section 310 includes input devices such as a touch panel, a button, and a microphone. When the start of imaging is instructed, the input section 310 may notify the control circuit 330 that the start of imaging has been instructed.

The output section 320 includes an output device such as a display or a speaker. The output section 320 displays a notification regarding the setting of the mode by the control circuit 330. Alternatively, a sound related to the setting of the mode is output.

Upon detecting that charging has started, the power supply section 142 may notify the control circuit 330 that the battery has started supplying power, that the battery has been connected to a commercial power supply, or that the battery has been disconnected from a commercial power supply.

When the built-in sensor detects that the handle 143 is held by a person, the control circuit 330 may be notified.

The control circuit 330 controls the entire medical cart 100. The control circuit 330 may be instructed to start imaging from the input section 310. The control circuit 330 may be notified by the power supply section 142 that charging has started, that the battery has started supplying power, that the power supply section has been connected to a commercial power supply, or that the power supply section has been disconnected from a commercial power supply. The control circuit 330 may be notified, from a sensor built in the handle 143, that it has been held by a person. The control circuit 330 may be notified that the fixer has been released, that information has been acquired from the RIS, that the communication method has been set to the wireless method, that movement has been detected, that a predetermined distance has been traveled, that a predetermined time has elapsed since the start of movement, and that the fixing unit has been locked.

The control circuit 330 is implemented as a computer, such as a central processing unit (CPU), an application specific integrated circuit (ASIC), or a field programmable gate array (FPGA). The control circuit 330 can manage the mode of the medical cart 100 and set the mode. The control circuit 330 can select and switch at least a fluoroscopy mode used as a fluoroscopy apparatus or a general imaging mode used as a general imaging apparatus. The control circuit 330 may be capable of selecting an imaging mode from three or more modes including other modes. Hereinafter, a mode used as a general imaging apparatus is referred to as a general imaging mode. The general imaging mode may be a dynamic imaging mode used as a dynamic imaging apparatus. The radiation dose allowed in the dynamic imaging mode is less than the radiation dose allowed in the fluoroscopy mode. The control circuit 330 may rotate and move the vertical arm 131 and the horizontal arm 132.

When the current mode is the fluoroscopic mode, the control circuit 330 restricts the use outside the management area.

The restriction of the use outside the management area may be supported by so-called intangible support, which provides a notification, a warning, or the like to a user such as a radiologist who handles the medical cart 100 to promote the restriction of the use, or may be supported by so-called tangible support, which prevents a high dose (a radiation dose exceeding an allowable radiation dose outside the management area) of radiation from being output from the medical cart 100 outside the management area or prevents the medical cart 100 from being able to exit the management area. It is sufficient to perform at least one of intangible support and tangible support, and both may be performed.

For tangible support, the control circuit 330 can perform at least one of control over the building and control over the medical cart 100.

The use of the medical cart 100 may be restricted by the building or the medical cart 100. At least one of the building and the medical cart 100 needs to perform the processing, or both of them may perform the processing.

As the control executed by the building, a door of the management area may be locked to prevent the medical cart 100 from exiting the management area.

The control executed by the medical cart 100 may be control such that the medical cart 100 cannot exit the management area when irradiation with a radiation dose equal to or more than the allowable radiation dose is possible, or control such that the radiation generation apparatus 110 is prohibited from emitting the radiation at a radiation dose exceeding the allowable radiation dose outside the management area.

Figure 10:
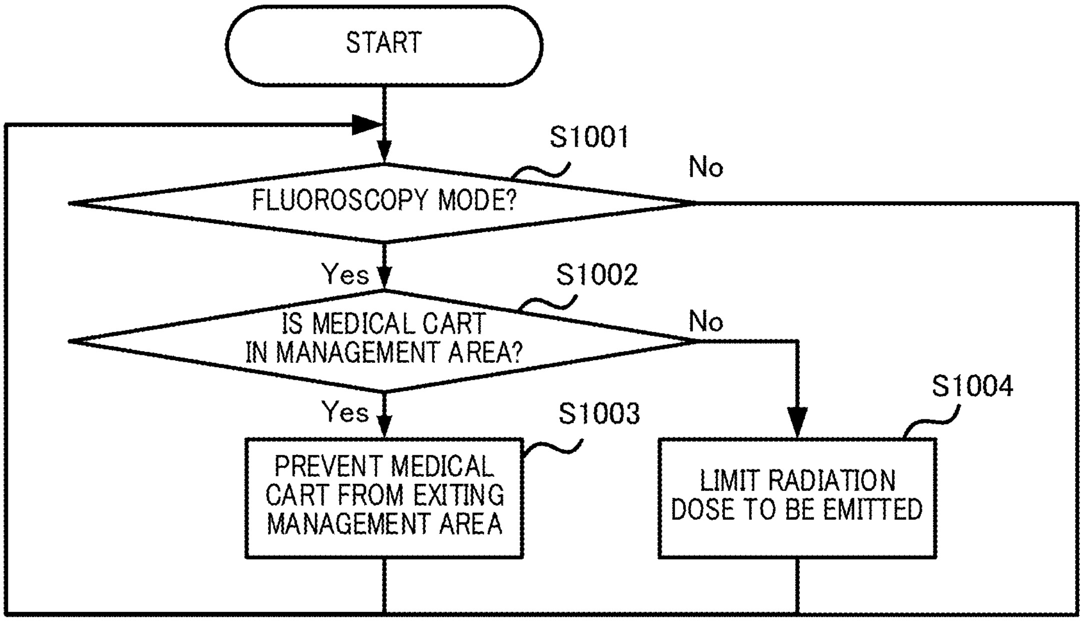
FIG. 10 is a flowchart of processing executed by the control device.

FIG. 10 illustrates a flowchart of processing executed by the control device. For example, the control device may be the control circuit 330 of the medical cart 100. The control device may be located anywhere. The flowchart may be executed at predetermined intervals (for example, at regular time intervals), may be executed when some operation is performed on the medical cart 100, or may be executed at predetermined intervals and when some operation is performed. The execution of the flowchart illustrated in FIG. 10 by the medical cart 100 can prevent emission of the radiation exceeding the allowable radiation dose outside the management area.

The control circuit 330 determines whether the imaging mode set in the medical cart 100 is the fluoroscopy mode (step S1001).

When the medical cart 100 is not in the fluoroscopy mode (e.g., the dynamic imaging mode) (step S1001, No), the control circuit 330 returns to step S1001 and determines the mode of the medical cart 100. The control circuit 330 can similarly determine an imaging mode in which radiation can be emitted only in the management area, other than the fluoroscopy mode.

When the medical cart 100 is in the fluoroscopy mode (step S1001, Yes), the control circuit 330 determines whether the radiation generation apparatus 110 (the medical cart 100) is located inside the management area (step S1002).

When the medical cart 100 is located inside the management area (step S1002, Yes), the control circuit 330 performs processing of preventing the medical cart 100 from exiting the management area (step S1003). Processing for prompting the user not to exit the management area may be executed. Details will be described later.

When the medical cart 100 is located outside the management area (step S1002, No), the control circuit 330 limits the radiation dose emitted by the radiation generation apparatus 110 (medical cart 100) (step S1004). For example, the control circuit 330 may prohibit the radiation generation apparatus 110 from emitting a radiation dose exceeding the allowable radiation dose. Processing for prompting the user to limit the radiation dose emitted by the radiation generation apparatus 110 may be executed. This case will be described in detail later.

The control circuit 330 may execute the processing of step S1004 when determining that the medical cart 100 has started moving even when the medical cart 100 is located inside the management area. The control circuit 330 may perform the processing in both steps S1003 and S1004 when the medical cart 100 starts moving in the management area. After execution of the processing in step S1003 or step S1004, the processing returns to step S1001.

For example, at least one of the following (1) to (8) may be executed as the control on the medical cart 100.

(1) When the fluoroscopy mode is set, the medical cart 100 is locked (not movable).

(2) Outside the management area, the medical cart 100 is shut down (powered off).

(3) Outside the management area, power supply to the medical cart 100 is stopped.

(4) Outside the management area, the supply of power to the radiation generation apparatus 110 is cut (shut down).

(5) Outside the management area, the mode of the medical cart 100 is switched to the dynamic imaging mode.

(6) Outside the management area, the fluoroscopy mode of the medical cart 100 is disabled.

(7) The radiation dose emitted by the medical cart 100 is limited to the output range in the area where the medical cart 100 is located. For example, outside the management area, the radiation generation apparatus 110 is prevented from emitting radiation exceeding the upper limit (the allowable radiation dose). For example, the irradiation time in the fluoroscopy mode may be limited.

(8) The fluoroscopy mode cannot be set outside the management area. For example, the fluoroscopy mode is grayed out on the setting screen of the medical cart 100.

As intangible support, the control circuit 330 may cause the output section 320 to provide a notification regarding the current mode (i.e., the medical cart 100 may output a warning), or may cause a building to output a warning. The warning may be at least one of a notification regarding the current mode and a notification that the vehicle is outside the management area.

In the dynamic imaging mode, the control circuit 330 may cause the output section 320 to issue a warning when the imaging condition set in advance by the input section 310 is an imaging condition that is not accepted as a general imaging apparatus.

[Determination of Position of Medical Cart]

Whether the medical cart 100 is inside or outside the management area may be determined by the medical cart 100 or by a control device (hereinafter referred to as a "building control device") that controls a building (for example, a door of the management area). For example, the building control device may be installed in the building, or the control circuit 330 of the medical cart 100 may be the building control device.

A global navigation satellite system (GNSS) such as a global positioning system (GPS) mounted on the medical cart 100 may be used to determine whether the medical cart 100 is located inside the management area or outside the management area.

By the communicator 144 of the medical cart 100 communicating with a communication device (hereinafter referred to as a "building communication device") installed inside the management area, it may be determined that the medical cart 100 is located inside or outside the management area.

For example, when the medical cart 100 receives a signal (e.g., a beacon signal) transmitted from a building communication device installed inside the management area, it may be determined that the medical cart 100 is located inside the management area, or when the medical cart 100 receives a signal (e.g., a beacon signal) transmitted from a building communication device installed outside the management area, it may be determined that the medical cart 100 is located outside the management area. Different beacon signals may be transmitted from both the inside and the outside of the management area, and whether the medical cart 100 is located inside the management area or outside the management area may be determined according to which of the beacon signals the medical cart 100 receives.

For example, when a building communication device installed in each place in the building receives a signal (e.g., a beacon signal) transmitted from the medical cart 100, the building communication device can recognize that the medical cart 100 is located at the installation place of the building communication device, and thus the building control device can determine whether the medical cart 100 is located inside the management area or outside the management area.

A sensor such as a camera mounted on the medical cart 100 may be used to determine whether the medical cart 100 is inside or outside the management area.

The building control device may determine whether the medical cart 100 is located inside the management area or outside the management area using a sensor such as a camera installed in the building.

When the medical cart 100 determines whether the medical cart 100 is inside or outside the management area, the medical cart 100 may notify the building control device. When the building control device determines whether the medical cart 100 is located inside or outside the management area, the building control device may notify the medical cart 100. Communication between the building control device and the control circuit 330 of the medical cart 100 allows either of the control devices to control the building (e.g., lock the door) and/or the medical cart 100. Another control device (e.g., a central management device) may communicate with the control circuit 330 of the medical cart 100 and/or the building control device to control the building (e.g., lock the door) and/or the medical cart 100. That is, the control device may be located anywhere.

[Operation 1]

First, a description is given of operation performed when the control circuit 330 causes the output section 320 to provide notification regarding the current mode.

The imaging conditions are set by the input section 310, and the set imaging conditions are applied to the generator 111 under the control of the input section 310, whereby the radiation generation apparatus 110 generates radiation.

In the dynamic imaging mode, imaging conditions are set by the input/output section 141 such that emission of pulsed radiation is repeated a plurality of times per predetermined time (for example, 15 times per second) for each instruction of the input/output section 141 until the duration is reached.

In a case where the radiation generation apparatus 110 cannot repeat the emission of pulsed radiation a plurality of times per predetermined time, the emission of radiation may be continued for a predetermined time. The phrase "emitting radiation for a predetermined time" in the present disclosure includes both pulsed emission in which emission of pulsed radiation is repeated a plurality of times over a predetermined time and continuous emission in which radiation is continuously emitted for a predetermined time. The duration is, for example, 15 seconds. In the dynamic imaging mode, when emission is instructed by the emission instruction switch, radiation is emitted with the duration as the maximum emission time. That is, in the dynamic imaging mode, radiation is emitted within the duration when the emission instruction switch is operated.

The intensity of radiation in the dynamic imaging mode may be lower than the intensity of radiation in the fluoroscopy mode.

In the dynamic imaging mode, the amount of radiation emitted in one pulse may be less than the amount of radiation emitted in a case in which a still image is captured, and therefore, the radiation dose applied to the patient as a whole can be made similar to that in a case in which a still image of the chest is captured. Note that in the case of continuous emission of radiation, it is desirable to set imaging conditions that do not significantly increase the amount of exposure of the patient.

In the fluoroscopy mode, imaging conditions are set in the radiation generation apparatus 110 by the input section 310 under the control of the control circuit 330 such that emission of pulsed radiation is repeated a plurality of times per predetermined time (for example, 15 times per second) based on the operation of the emission button. In the fluoroscopy mode, the duration does not have to be set. In the fluoroscopic mode, a longer duration may be set than in the dynamic imaging mode.

In a case where the radiation generation apparatus 110 cannot repeat the emission of pulsed radiation a plurality of times per predetermined time, the emission of radiation may be continued for a predetermined time. In the fluoroscopy mode, radiation is emitted while emission is instructed by the emission button. That is, in the case where no duration is set in the fluoroscopy mode, radiation is emitted without any time limit while an emission instruction is being provided.

The control circuit 330 sets various imaging conditions (a tube voltage, a tube current, an emission time, a tube current-time product (mAs value), an imaging site, an imaging direction, and the like) at least for the radiation generation apparatus 110 on the basis of input from the input section 310. The control circuit 330 may set various imaging conditions for the radiation detection apparatus 120. The control circuit 330 may set various imaging conditions on the basis of imaging order information acquired from another system (HIS, RIS, or the like) or a user (e.g., a technician). The control circuit 330 may set various imaging conditions in the radiation generation apparatus 110 and/or the radiation detection apparatus 120, for example, based on imaging order information or a table in which users and various imaging conditions are associated with each other.

In a case where the set various imaging conditions do not satisfy use as a general imaging device and the current mode notified from the control circuit 330 is the general imaging mode, the control circuit 330 may cause the output section 320 to provide a warning.

[Mode]

The medical cart 100 has a plurality of modes, for example, a general imaging mode and a fluoroscopy mode. Three or more modes may be provided. The general imaging mode may be a dynamic imaging mode. The mode may be set by input from the input section 310. The mode may be set by being selected from a plurality of imaging modes displayed on the output section 320. The mode may be set by the switch. The imaging mode of the medical cart 100 may be set according to a patient to be imaged, an examination order, or an imaging order.

The radiation dose emitted in the dynamic imaging mode may be different from the radiation dose emitted in the fluoroscopy mode. The radiation dose emitted in the fluoroscopy mode may be greater than the radiation dose emitted in the dynamic imaging mode.

Furthermore, while there is a radiation time in the dynamic imaging mode, there is no radiation time in the fluoroscopy mode. That is, although the medical cart 100 does not emit radiation after the emission time elapses even when the medical cart 100 continues to output the emission instruction in the dynamic imaging mode, the medical cart 100 emits radiation all the time while the medical cart 100 outputs the emission instruction in the fluoroscopy mode.

In a case where the fluoroscopy mode is set, the control circuit 330 may cause the input/output section 141 to display the moving image generated by the radiation detection apparatus 120 in real time. When the dynamic imaging mode is set, the control circuitry 330 may cause the input/output section 141 to display a moving image that is more limited than a moving image displayed when the fluoroscopy mode is set. When the dynamic imaging mode is set, the input/output section 141 may display, for example, a moving image delayed relative to a case where the fluoroscopy mode is set. When the dynamic imaging mode is set, for example, the input/output section 141 may perform display at a frame rate lower than that when the fluoroscopy mode is set. The control circuit 330 may restrict a moving image generated by the radiation detection apparatus 120 or may cause the radiation detection apparatus 120 to restrict a moving image to be generated.

The control circuit 330 causes the input/output section 141 to display a moving image corresponding to the set mode, so that the X-ray imaging apparatus can be used as a fluoroscopy apparatus in a management area and as a dynamic imaging apparatus in a general hospital room or the like. The radiation dose allowed in the dynamic imaging mode is less than the radiation dose allowed in the fluoroscopy mode.

[Notification of Mode]

Since the dynamic imaging mode is used as a general imaging apparatus, the dynamic imaging mode can be used in a general hospital room. However, since the fluoroscopy mode is used as a fluoroscopy apparatus, a place where the fluoroscopy mode can be used is strictly limited, and the fluoroscopy mode cannot be used in a general hospital room. That is, the medical cart 100 can be used in the fluoroscopy mode in a specific place, but is required to be used in the dynamic imaging mode in other places according to the Japanese law.

Therefore, the medical cart 100 includes the input/output section 141 and provides notification about the mode. The output section 320 may provide a notification prompting the user to set the mode from the fluoroscopy mode to the dynamic imaging mode. The output section 320 may issue a notification for prompting the setting from the dynamic imaging mode to the fluoroscopy mode.

[Timing of Notification]

The medical cart 100 may provide the notification before movement of the medical cart 100 or at the start of the movement. Since the medical cart 100 is often moved after the setting, it is effective that the notification is provided before the movement and/or at the start of the movement. For example, the medical cart 100 may provide the notification when acquiring the imaging information from the RIS. The medical cart 100 may make a notification based on whether the acquired imaging information indicates fluoroscopy or dynamic imaging. For example, the operation may be performed when the fixer of the medical cart 100 is unlocked. Since the medical cart 100 moves after the lock is released, it can be said that the medical cart 100 has not moved yet when the lock is released. For example, the medical cart 100 may provide a notification when movement of the medical cart 100 is detected. Detection of movement of the medical cart 100 may be performed by detection of rotation of the wheels 145. For example, the medical cart 100 may provide a notification when the power supply section 142 is disconnected from the commercial power supply and the battery starts supplying power. For example, the medical cart 100 may issue a notification when the main body 140 is turned on and the power supply section 142 starts supplying power. For example, the medical cart 100 may make the notification when the communication method of the medical cart 100 is set from wired communication to wireless communication. For example, the medical cart 100 may issue a notification when detecting that the handle 143 is held.

The medical cart 100 may make the notification while the medical cart 100 is moving. The medical cart 100 may provide a notification, for example, when the medical cart 100 has moved a predetermined distance. For example, the medical cart 100 may issue a notification when a predetermined time has elapsed since the medical cart 100 started moving.

The medical cart 100 may provide the notification after the medical cart 100 moves. The medical cart 100 may provide the notification, for example, when the power supply section 142 is connected to a commercial power supply. The medical cart 100 may provide the notification when, for example, a switch of the main body 140 is operated and the power supply section 142 starts supplying power. The medical cart 100 may, for example, provide the notification when the fixer is locked.

The medical cart 100 may provide the notification when the medical cart 100 starts imaging. The medical cart 100 may provide the notification, for example, when the start of imaging is instructed from the input section 310. After the notification, the imaging may be started after the mode is confirmed.

[Notification Method]

For example, the notification of the medical cart 100 is provided by output to the input/output section 141. When the input/output section 141 is divided into the input section 310 and the output section 320, the processing may be performed by the output to the output section 320. The output section 320 may perform notification by display on a monitor, for example. The output section 320 may provide the notification by, for example, turning on an indicator light of the main body 140. The color of the indicator light may be changed according to the current mode. For example, the output section 320 may perform notification by locking of the fixer. The output section 320 may provide a notification by voice, for example. For example, the output section 320 may perform notification by vibration of the main body 140 or a part of the main body 140. In a case where the main body 140 is provided with a handle, the output section 320 may perform notification by vibration of the handle.

The notification may be provided using a plurality of notification methods. For example, display on a monitor and notification by voice may be performed. For example, all of the display on the monitor, the turning on of the indicator light, the notification by sound, and the vibration of the handle may be performed.

[Notification Content]

The notification regarding the setting of the mode may indicate that the fluoroscopy mode has been selected. The notification regarding the setting of the mode may be to select the dynamic imaging mode or the general imaging mode. The notification related to the setting of the mode may be a notification of the current mode. The notification regarding the setting of the mode may be a notification prompting the user to confirm the current mode. The notification related to the setting of the mode may be that the setting of the mode has been completed. The notification regarding the setting of the mode may be a notification that the mode is being set. The medical cart 100 may notify whether the imaging information acquired from the RIS indicates fluoroscopy or dynamic imaging.

Figure 4:
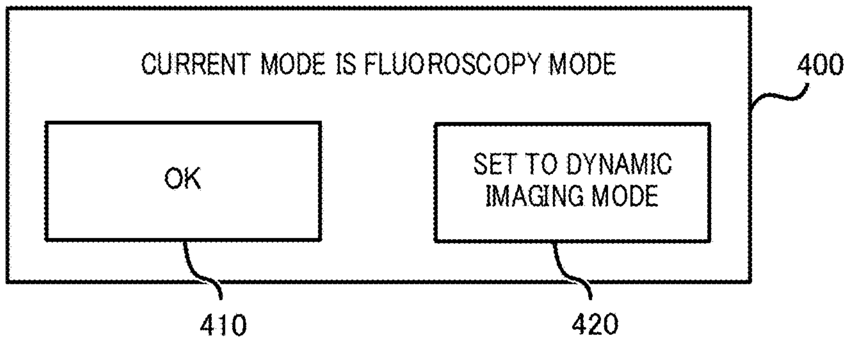
FIG. 4 is a diagram illustrating an example of a window displayed on the screen in a case where the current mode is the fluoroscopy mode.

FIG. 4 is a diagram illustrating an example window 400 displayed on the screen in a case of providing notification that the current mode is the fluoroscopy mode. The color of window 400 may be changed in accordance with the mode to be notified. Displaying the current mode or providing a notification of the fluoroscopy mode can promote setting to the dynamic imaging mode.

In a case where the current mode is the fluoroscopy mode, a button for giving an instruction to set to the dynamic imaging mode may be displayed. The size of the button 410 of "OK" may be different from the size of the button 420 of "set to dynamic imaging mode". The button 410 may have a size smaller than a size of the button 420. The size of the button 410 may be the same as the size of the button 420.

When the current mode is the dynamic imaging mode, the button for giving an instruction to set to the fluoroscopy mode may be displayed in a smaller size than the size of the button "OK". The button for instructing the setting to the fluoroscopy mode does not have to be displayed.

Since the size of the button for maintaining the fluoroscopy mode is reduced, the operator needs to carefully perform the confirmation operation when the mode is used as the fluoroscopy mode, and therefore, the confirmation operation when the mode is used as the fluoroscopy mode can be carefully performed.

By not displaying the button for instructing the setting to the fluoroscopy mode or by using a button of a small size, it is possible to reduce the possibility of setting to the fluoroscopy mode by an erroneous operation, and thus it is possible to prevent exposure due to an erroneous operation.

Figure 5:
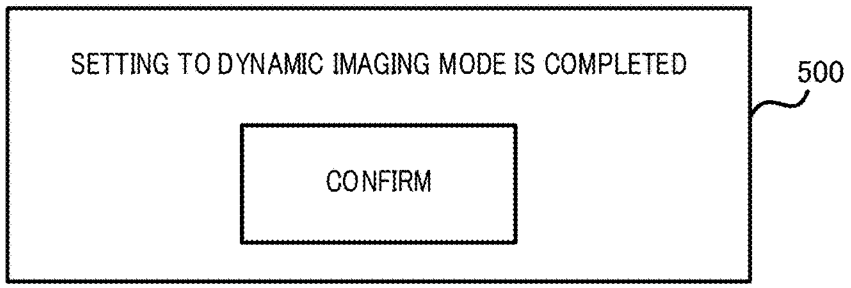
FIG. 5 is a diagram illustrating an example of a window to be displayed on a screen in the case of notifying that setting to the dynamic imaging mode has been completed.

FIG. 5 is a diagram illustrating an example window 500 displayed on a screen for providing a notification that setting to the dynamic imaging mode has been completed. The color of the window 500 may be changed according to the mode after completion.

Figure 6:
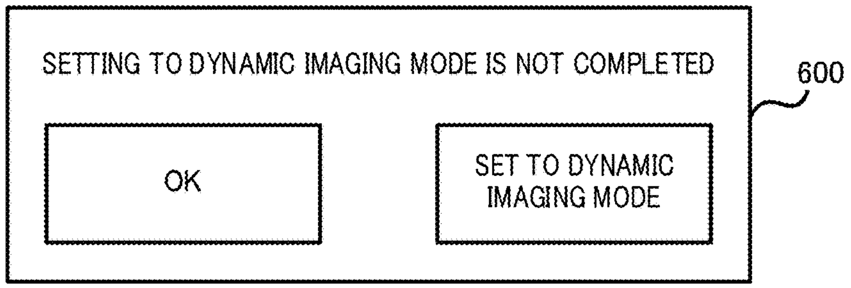
FIG. 6 is a diagram illustrating an example of a window displayed on a screen in the case of notifying that the setting to the dynamic imaging mode is not completed.

FIG. 6 is a diagram illustrating an example window 600 to be displayed on a screen for providing a notification that setting to the dynamic imaging mode is not completed. The color of the window 600 may be different from the color of the window 500. By notifying that the setting to the dynamic imaging mode is not completed, it is possible to prompt the setting to the dynamic imaging mode.

[Flowchart]

Figure 9:
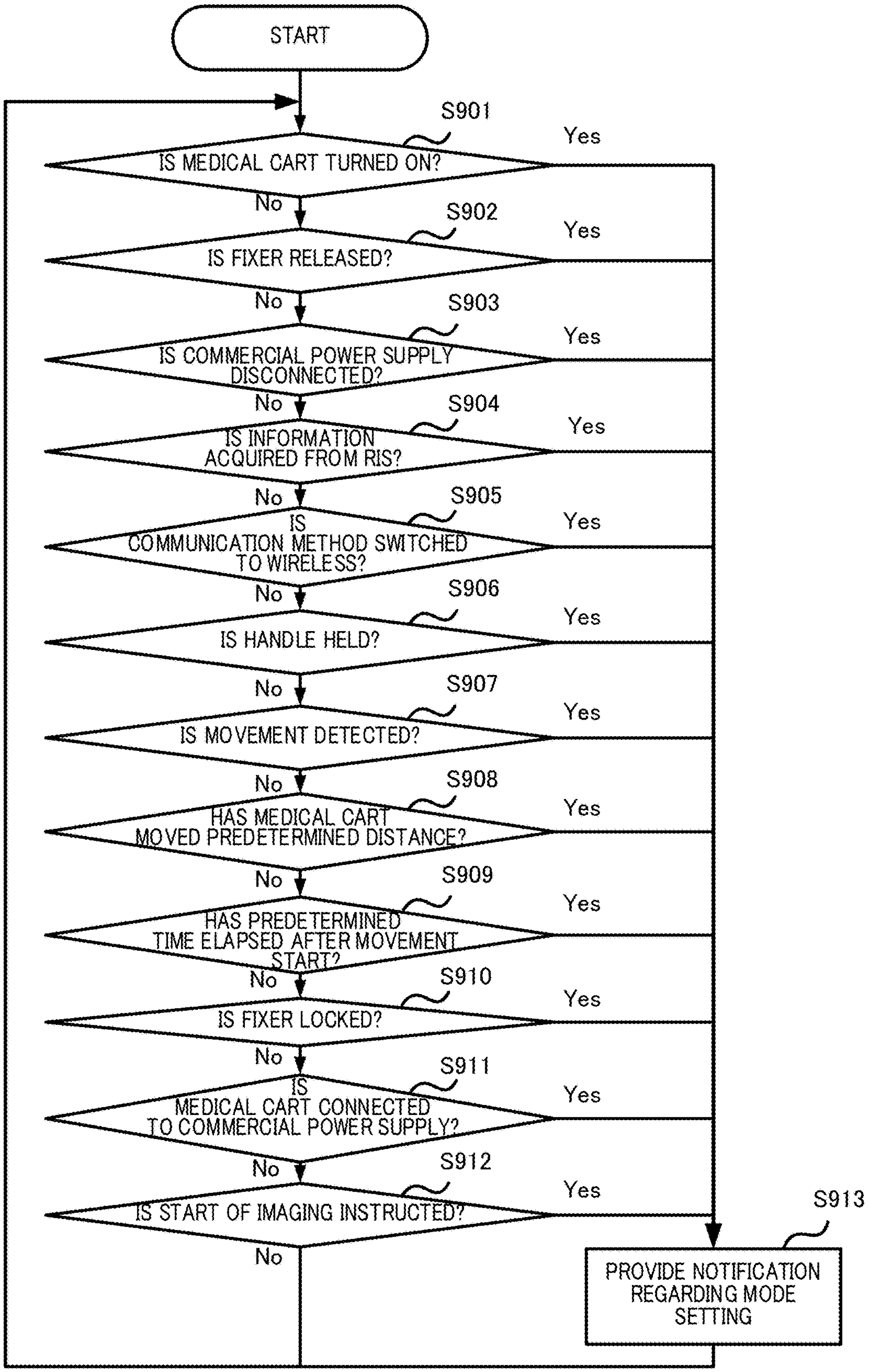
FIG. 9 is a flowchart of processing executed by the control circuit.

FIG. 9 is a diagram illustrating an example of a flowchart of processing performed by the control circuit 330. FIG. 9 determines when to output a warning. The control circuit 330 performs control according to the state of the medical cart 100.

The control circuit 330 determines whether the medical cart 100 has been turned on (step S901). Upon determination that the medical cart 100 has been turned on, the control circuit 330 performs the processing of step S913. Upon determination that the medical cart 100 is not turned on, the control circuit 330 performs the processing of step S902.

The control circuit 330 determines whether the fixer of the medical cart 100 has been released (step S902). Upon determining that the fixer of the medical cart 100 has been released, the control circuit 330 performs processing in step S913. When determining that the fixer of the medical cart 100 is not released, the control circuit 330 performs the processing of step S903.

The control circuit 330 determines whether the medical cart 100 has been disconnected from the commercial power supply (step S903). The control circuit 330 may determine whether the battery of the medical cart 100 has started supplying power. Upon determination that the medical cart 100 has been disconnected from the commercial power supply, the control circuit 330 performs the processing of step S913. Upon determination that the medical cart 100 has not been disconnected from the commercial power supply, the control circuit 330 performs the processing of step S904.

The control circuit 330 determines whether the medical cart 100 has acquired imaging information from the RIS (step S904). The control circuit 330 may make the determination based on the content of the acquired imaging information. Upon determination that the medical cart 100 has acquired imaging information from the RIS, the control circuit 330 performs the processing of step S913. When determining that the medical cart 100 has not acquired imaging information from the RIS, the control circuit 330 performs the processing of step S905.

The control circuit 330 determines whether the communication method used by the medical cart 100 has been set from wired communication to wireless communication (step S905). When the control circuit 330 determines that the communication method used by the medical cart 100 has been set from wired communication to wireless communication, the control circuit 330 performs the processing of step S913. When determining that the communication method used by the medical cart 100 has not been set from wired communication to wireless communication, the control circuit 330 performs the processing of step S906.

The control circuit 330 determines whether the handle of the medical cart 100 has been held (step S906). Upon determination that the handle of the medical cart 100 has been held, the control circuit 330 performs the processing of step S913. When determining that the handle of the medical cart 100 is not held, the control circuit 330 performs the processing of step S907.

The control circuit 330 determines whether movement of the medical cart 100 has been detected (step S907). The control circuit 330 may detect the movement of the medical cart 100 by detecting the rotation of the wheel 145. When determining that the movement of the medical cart 100 has been detected, the control circuit 330 performs the processing of step S913. When determining that the movement of the medical cart 100 has not been detected, the control circuit 330 performs the processing of step S908.

The control circuit 330 determines whether the medical cart 100 has moved a predetermined distance (step S908). The control circuit 330 may detect, based on the number of rotations of the wheel 145, that the medical cart 100 has moved a predetermined distance. When determining that the medical cart 100 has moved the predetermined distance, the control circuit 330 performs the processing of step S913. When the control circuit 330 determines that the medical cart 100 has not moved the predetermined distance, the control circuit 330 performs the processing of step S909.

The control circuit 330 determines whether a predetermined time has elapsed since the start of the movement of the medical cart 100 (step S909). When the control circuit 330 determines that the predetermined time has elapsed after the start of the movement of the medical cart 100, the control circuit 330 performs the processing of step S913. When the control circuit 330 determines that the predetermined time has not elapsed since the start of the movement of the medical cart 100, the control circuit 330 performs the processing of step S910.

The control circuit 330 determines whether the fixer of the medical cart 100 has been locked (step S910). Upon determining that the fixer of the medical cart 100 has been locked, the control circuit 330 performs processing in step S913. When determining that the fixer of the medical cart 100 is not locked, the control circuit 330 performs the processing of step S911.

The control circuit 330 determines whether the medical cart 100 has been connected to a commercial power supply (step S911). Upon determination that the medical cart 100 has been connected to the commercial power supply, the control circuit 330 performs the processing of step S913. When determining that the medical cart 100 is not connected to the commercial power supply, the control circuit 330 performs the processing of step S912.

The control circuit 330 determines whether the medical cart 100 has been instructed to start imaging (step S912). Upon determining that the medical cart 100 has been instructed to start imaging, the control circuit 330 performs processing in step S913. When the control circuit 330 determines that the start of imaging has not been instructed to the medical cart 100, the processing returns to step S901.

The control circuit 330 causes the input/output section 141 to provide a notification regarding the setting of the imaging mode (step S913). That is, in a case where Yes is determined in any of the steps from S901 to S912, notification regarding the setting of the imaging mode is performed. The display form may be changed depending on which step is determined to be Yes.

In a case where the input/output section 141 is caused to perform the notification in step S913, and in a case where No is determined in all of the steps from step S901 to step S912, the processing returns to step S901.

Some of the steps from step S901 to step S912 does not have to be performed.

The "notification related to setting of imaging mode" may be a notification about the processing performed in step S1003 in FIG. 10, for example, "door has been locked" or a notification about the processing performed in step S1004 in FIG. 10, for example, "the radiation dose has been limited". The "notification related to setting of imaging mode" may be output from the output section 320 of the medical cart 100 or output from an output device installed in the building. The "notification related to the setting of the imaging mode" may include a plurality of contents. For example, the notification may be "Fluoroscopy mode is set. Please lock the door."

[Operation 2]

Next, an operation in a case where the building is caused to output a warning will be described.

The building control device recognizes whether the medical cart 100 is located inside the management area or outside the management area.

The building control apparatus may determine whether the medical cart 100 is inside or outside the management area, or the medical cart 100 may transmit the determination result to the building control apparatus. In addition, the building control device may recognize the state of the medical cart 100 (mode, location, movement status, etc) by receiving the state from the communicator 144.

For example, the building control device may output a warning in the building according to the recognized state of the medical cart 100. The warning may be the same as the warning of the medical cart 100. For example, the mode of the medical cart 100 may be displayed on a display installed in the management area. For example, when the medical cart 100 set to the fluoroscopy mode is located outside the management area, the building control device may turn on a buzzer installed outside the management area. For example, when the medical cart 100 set to the fluoroscopy mode is located inside the management area, a message such as "Lock the door" may be output from an output device (for example, a display or a speaker) in the management area. The warning issued by the building control device and the warning issued by the medical cart 100 may be the same or different. For example, the control circuit 330 of the medical cart 100 may output "Fluoroscopy mode is set" from the display of the medical cart 100, and the building control device may output "Please lock the door" from the speaker in the management area. For example, the sound output by the building control device and the sound output by the output section 320 of the medical cart 100 may have different tones.

[Operation 3]

Next, tangible support of the medical cart 100 will be described.

The medical cart 100 recognizes whether the medical cart 100 is inside the management area or outside the management area. The medical cart 100 may determine whether the medical cart 100 is located inside the management area or outside the management area. Alternatively, the building management device may determine whether the medical cart 100 is located inside the management area or outside the management area, and the medical cart 100 may recognize the location by receiving the determination result of the building management device from the communicator 144.

When the control circuit 330 recognizes that the medical cart 100 set to the fluoroscopy mode is located inside the management area, the control circuit 330 prevents the medical cart 100 from moving outside the management area. For example, the control circuit 330 controls a fixer (not illustrated) to fix the wheel 145 of the medical cart 100. For example, the control circuit 330 controls a fixer (not illustrated) to fix the medical cart 100 to a wire fixed to a wall forming the management area. The movement of the medical cart 100 is limited to the range of the wire. The control circuit 330 executes at least one of fixation of the wheel 145 and fixation of the wire.

When the medical cart 100 is set to the fluoroscopy mode, the control circuit 330 may prevents the medical cart 100 from moving. In this case, the fluoroscopy mode is set at the place where the medical cart 100 is used.

When the medical cart 100 recognizes that the medical cart 100 is located outside the management area, the medical cart 100 restricts radiation outside the management area. For example, at least one of the following (1) to (7) is executed.

(1) The control circuit 330 shuts down (powers off) the medical cart 100. Upon moving out of the management area, the medical cart 100 is temporarily powered off. For example, when the dynamic analysis mode is set as the default of the medical cart, the dynamic analysis mode can be set when the medical cart 100 is turned on. Instead of shutdown, reset may be performed. In addition, since it is necessary to newly perform the setting, it is possible to prevent radiation in the previous setting (for example, fluoroscopy mode).

(2) The control circuit 330 stops supplying power to the medical cart 100. When the power supply to the medical cart 100 is stopped, the medical cart 100 operates on the power of the storage battery. For example, since the power of the storage battery is not large, when the storage battery is set to not be able to emit radiation in the fluoroscopy mode, it is possible to prevent radiation in the fluoroscopy mode.

(3) The control circuit 330 cuts off (shuts down) power supply to the radiation generation apparatus 110. By cutting off the power supply to the radiation generation apparatus 110, radiation in the fluoroscopy mode can be prevented. When the medical cart 100 is set to the dynamic analysis mode or is recognized as being present in the management area, the supply of power to the radiation generation apparatus may be resumed.

(4) The control circuit 330 switches the mode of the radiation generation apparatus 110 to the dynamic imaging mode. For example, upon recognizing that the medical cart 100 is outside the management area, the control circuit 330 forcibly sets (changes) the mode of the radiation generation apparatus 110 to the dynamic imaging mode.

(5) The control circuitry 330 disables the fluoroscopy mode. For example, upon recognizing that the medical cart 100 is outside the management area, the control circuit 330 does not cause the radiation generation apparatus 110 to operate in the fluoroscopy mode.

(6) The control circuit 330 prevents the radiation generation apparatus 110 from emitting radiation exceeding an upper limit (allowable radiation dose). The control circuit 330 may change (e.g., lower) the upper limit (the allowable radiation dose). For example, the control circuitry 330 restricts the irradiation time in the fluoroscopy mode to prevent radiation exceeding the allowable radiation dose from being emitted.

(7) The control circuitry 330 prevents the setting of the fluoroscopy mode. For example, the control circuit 330 grays out the fluoroscopy mode on the setting screen of the medical cart 100. When the medical cart 100 is determined to be in the management area, the control circuit 330 may be able to change the mode to the fluoroscopy mode.

The control circuit 330 can prevent emission of radiation exceeding the allowable radiation dose (upper limit) outside the management area by restricting emission of radiation outside the management area.

[Operation 4]

Next, tangible support of a building will be described.

The building control device recognizes whether the medical cart 100 is located inside the management area or outside the management area, and whether the mode is the fluoroscopy mode or the general imaging mode. The building control device may determine whether the medical cart 100 is inside or outside the management area. Alternatively, the medical cart 100 may determine whether the medical cart 100 is inside or outside the management area, and the building control device may recognize the result by receiving the determination of the medical cart 100. The building control device receives information indicating whether the mode is the fluoroscopy mode or the general imaging mode from the medical cart 100, and thus recognizes whether the medical cart 100 is in the fluoroscopy mode or the general imaging mode.

The building control device controls the key of the door forming the management area according to the state of the medical cart 100. For example, when the medical cart 100 is located inside the management area and the fluoroscopy mode is set, the building control device locks the door forming the management area. The building control device unlocks the door forming the management area when the medical cart 100 is located outside the management area or when the medical cart 100 located inside the management area is set to the dynamic imaging mode.

In a case where a plurality of the medical carts 100 are located, when at least one of the medical carts 100 is located inside the management area and is set to the fluoroscopy mode, the door forming the management area may be locked. When another medical cart 100 moves into the management area, the door may be temporarily unlocked.

Locking the door can prevent the medical cart 100 set in the fluoroscopy mode from moving out of the management area.

In addition, the wire fixed to the medical cart 100 may be fixed to or released from the wall forming the management area. By fixing the wire fixed to the medical cart 100 to the wall forming the management area, the movement of the medical cart 100 is limited to the range of the wire, so that the medical cart 100 can be prevented from moving out of the management area.

The building control device executes at least one of the control of the key of the door and the fixing or opening of the wire.

Modification Example

It is desirable that the control circuit 330 has a function of limiting the operation of the radiation button in the fluoroscopy mode. It is desirable that the control circuit 330 perform user authentication and allow only the authenticated user to operate the radiation button in the fluoroscopy mode. The user to be authenticated is a user for which authority is set by the hospital, such as a doctor or a radiology technician. The authentication can be performed using well-known authentication means such as an ID or an account, and a password, a staff certificate, and/or biometric authentication.

The control circuit 330 may perform user authentication. In a case where it is authenticated that the user is an authorized user, the control circuit 330 allows the mode to be changed to the fluoroscopy mode, and in a case where the user is not an authorized user, the control circuit 330 may allow only the operation in the dynamic imaging mode or does not have to allow all the operations. User authentication that enables an operation limited to the dynamic imaging mode may be performed.

The control circuit 330 may enable the change to the first mode in a case where an imaging order or an inspection order received from the RIS or the like is imaging or inspection using the fluoroscopy mode. The control circuit 330 may be set based on an imaging order or an inspection order received from the RIS. The control circuit 330 may cause the input/output section 141 to change the setting performed on the basis of the imaging order or the inspection order received from the RIS.

The building control device does not have to be installed in the building in which the management area is installed. For example, the control circuit 330 of the medical cart 100 may perform control, or a control device installed in another building may perform remote control.

The mode of the medical cart 100 may be automatically set by recognizing whether the medical cart 100 is located in a specific place where the fluoroscopy apparatus can be used or in a place where the fluoroscopy apparatus cannot be used but a general imaging apparatus can be used. When the mode of the medical cart 100 is set, or when it is recognized that the medical cart 100 is located in a place where a fluoroscopy device can be used, a notification regarding the setting of the mode may be provided by the input/output section 141.

In a case of setting to the fluoroscopy mode or in a case of being set to the fluoroscopy mode, a confirmation screen may be displayed.

The control circuit 330 may always perform the notification regarding the mode setting. The control circuit 330 may provide the notification by a plurality of notification means. For example, the control circuit 330 may cause the display lamp to always notify the user of the current mode, and may cause the monitor to display a notification when the medical cart 100 is instructed to start imaging.

Figure 7:
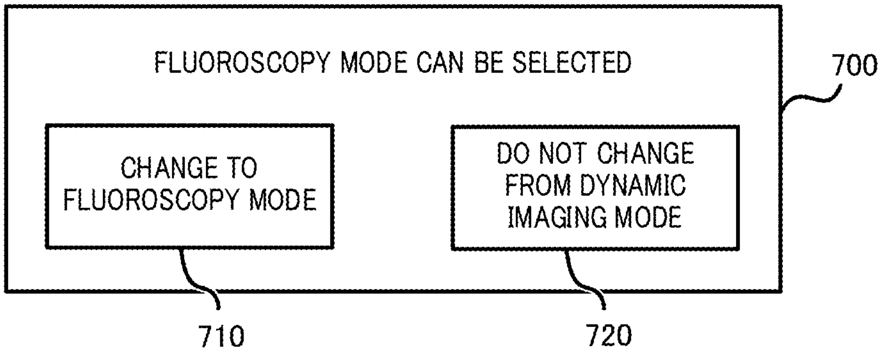
FIG. 7 is a diagram illustrating an example of a window displayed on the screen in a case where the fluoroscopy mode can be selected.

FIG. 7 is a diagram illustrating an example window 700 displayed on the screen in a case where the fluoroscopy mode can be selected.

The medical cart 100 may automatically set the fluoroscopy mode or the dynamic imaging mode according to the imaging information received from the RIS, and the input/output section 141 may provide a notification that the mode setting has been completed. The size of the button 710 for "change to fluoroscopic mode" may be different from the size of the button 720 for "remain in dynamic imaging mode and do not change". The size of the button 710 may be smaller than the size of the button 720. The size of the button 710 may be equal to the size of the button 720.

In a case of changing to the fluoroscopy mode, a confirmation window may be displayed.

Figure 8:
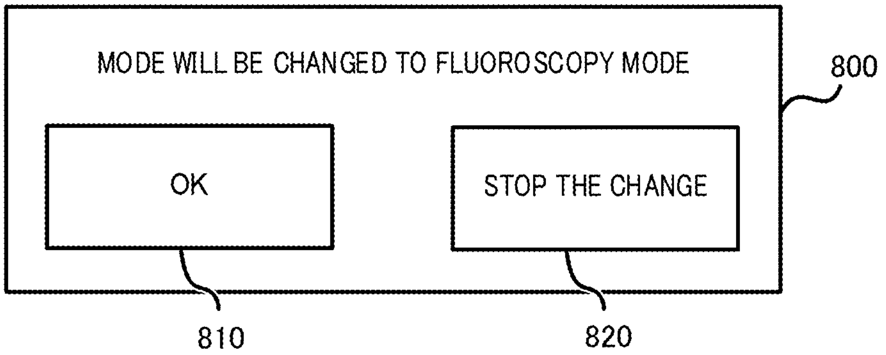
FIG. 8 is a diagram illustrating an example of a confirmation window when switching to the fluoroscopy mode.

FIG. 8 is a diagram illustrating an example confirmation window 800 in a case of changing to the fluoroscopy mode. In the window 800, the size of the button 810 (to be selected when the "fluoroscopy mode", which can only be used in limited locations) may be made smaller than the size of the button 820 (to be selected when the "dynamic imaging mode", which is used as a general imaging apparatus). Furthermore, the confirmation screen does not have to be displayed in the dynamic imaging mode, and the confirmation screen may be displayed in the fluoroscopy mode.

As the setting means causes the button to be selected when the mode is changed to the fluoroscopy mode as a smaller button than the button to be selected when the mode is changed to the dynamic imaging mode, more careful processing can be performed when the mode of the medical cart 100 is set to the fluoroscopy mode.

Furthermore, since the setting means allows the confirmation screen to be displayed only when the mode is set to the fluoroscopy mode, more careful processing can be performed when the mode of the medical cart 100 is set to the fluoroscopy mode.

Although the embodiments have been described above with reference to the drawings, the present disclosure is not limited to such examples. It is obvious that a person skilled in the art can conceive of various change examples or modification examples within the scope described in the claims. It is to be understood that such changes or modifications also belong to the technical scope of the present disclosure. Furthermore, the constituent elements in the embodiments may be combined as appropriate without departing from the spirit of the present disclosure.

(1) A mobile radiographic imaging system according to an embodiment of the present disclosure includes: a radiation generation apparatus that emits radiation and is configured to be set to a plurality of imaging modes including a first mode for performing fluoroscopic imaging and a second mode that is a general imaging mode, wherein a series of frame images is acquired by irradiating a subject with the radiation in the second mode; and a hardware processor configured to restrict use of the first mode outside a management area.

(2) A mobile radiographic imaging system according to an embodiment of the present disclosure is such that in the mobile radiographic imaging system of (1), the mobile radiographic imaging system is a medical cart; and the medical cart includes the radiation generation apparatus and the hardware processor.

(3) A mobile radiographic imaging system according to an embodiment of the present disclosure is such that in the mobile radiographic imaging system of (2), the hardware processor is at least one of (1) a hardware processor that controls the medical cart, and (2) a hardware processor that controls a building in which the management area is installed; and the hardware processor executes at least one of (1) outputting a warning to a user, and (2) causing the medical cart to restrict emission of the radiation outside the management area.

(4) A mobile radiographic imaging system according to an embodiment of the present disclosure is such that in the mobile radiographic imaging system of (3), the warning is output in at least one of cases below: (1) before movement of the medical cart and/or at a start of the movement, (2) when a fixer of the medical cart is released, (3) when the medical cart is disconnected from a commercial power supply, (4) when the medical cart acquires imaging information from a radiology information system (RIS), (5) when communication between a main body of the medical cart and the radiation detection apparatus is switched from wired communication to wireless communication, (6) when it is detected that a handle of the medical cart is held, (7) when the movement of the medical cart is detected, (8) during the movement of the medical cart, (9) when the medical cart has moved a predetermined distance, (10) when a predetermined time has elapsed since the start of the movement of the medical cart, (11) after the medical cart moves, (12) when the fixer of the medical cart is locked, (13) when the medical cart is connected to the commercial power supply, and (14) when a start of imaging is instructed.

(5) A mobile radiographic imaging system according to an embodiment of the present disclosure is such that in the mobile radiographic imaging system of (3), the warning is a notification by at least one of (1) displaying on a monitor, (2) turning on a light, and (3) outputting sound.

(6) A mobile radiographic imaging system according to an embodiment of the present disclosure is such that in the mobile radiographic imaging system of (2), the warning provides a notification of at least one of (1) a current mode being a fluoroscopy mode, (2) the current mode, and (3) mode setting having been completed.

(7) A mobile radiographic imaging system according to an embodiment of the present disclosure is such that in the mobile radiographic imaging system of (1), the hardware processor is a hardware processor that controls the medical cart, and executes at least one of (1) outputting a warning to a user, and (2) causing the radiation generation apparatus to restrict emission of the radiation outside the management area.

(8) A mobile radiographic imaging system according to an embodiment of the present disclosure is such that in the mobile radiographic imaging system of (6), when the radiation generation apparatus is set to the first mode, the hardware processor prevents the medical cart from moving outside the management area.

(9) A mobile radiographic imaging system according to an embodiment of the present disclosure is such that in the mobile radiographic imaging system of (7), the hardware processor executes at least one of (1) controlling a fixer configured to fix the medical cart, and (2) fixing the medical cart to a wire fixed to a wall forming the management area.

(10) A mobile radiographic imaging system according to an embodiment of the present disclosure is such that in the mobile radiographic imaging system of (6), when the radiation generation apparatus is located outside the management area, the hardware processor executes control to prohibit the radiation generation apparatus from emitting the radiation at a radiation dose exceeding an allowable radiation dose.

(11) A mobile radiographic imaging system according to an embodiment of the present disclosure is such that in the mobile radiographic imaging system of (9), when the hardware processor recognizes that the radiation generation apparatus is set to the first mode and the medical cart is located outside the management area, the hardware processor executes at least one of (1) shutting down the medical cart, (2) stopping power supply to the medical cart, (3) cutting off the power supply to the radiation generation apparatus, (4) switching a mode of the radiation generation apparatus to the second mode, (5) disabling the first mode, (6) preventing emission of the radiation exceeding the allowable radiation dose from the radiation generation apparatus, and (7) preventing setting of a fluoroscopy mode.

(12) A mobile radiographic imaging system according to an embodiment of the present disclosure is such that in the mobile radiographic imaging system of (1), the hardware processor is a hardware processor that controls a building in which the management area is installed, and executes at least one of (1) outputting a warning to a user, and (2) causing the radiation generation apparatus to restrict emission of the radiation outside the management area.

(13) A mobile radiographic imaging system according to an embodiment of the present disclosure is such that in the mobile radiographic imaging system of (11), when the medical cart is located inside the management area, the hardware processor executes at least one of (1) locking a key of a door forming the management area, and (2) fixing a wire fixed to the medical cart to a wall forming the management area.

(14) A method for restricting the mobile radiographic imaging system according to an embodiment of the present disclosure wherein in the mobile radiographic imaging system that is configured to be set to a plurality of imaging modes including a first mode for performing fluoroscopic imaging and a second mode that is a general imaging mode and wherein a series of frame images is acquired by irradiating a subject with the radiation in the second mode, use of the first mode is restricted outside a management area.

INDUSTRIAL APPLICABILITY

The present disclosure is useful for a radiographic imaging apparatus.

Although embodiments of the present invention have been described and illustrated in detail, the disclosed embodiments are made for purpose of illustration and example only and not limitation. The scope of the present invention should be interpreted by terms of the appended claims.

What is claimed is:

1. A mobile radiographic imaging system comprising:

a radiation generation apparatus that emits radiation and is configured to be set to a plurality of imaging modes including a first mode for performing fluoroscopic imaging and a second mode that is a general imaging mode, wherein a series of frame images is acquired by irradiating a subject with the radiation in the second mode; and a hardware processor configured to restrict use of the first mode outside a management area.

2. The mobile radiographic imaging system according to claim 1, wherein:

the mobile radiographic imaging system is a medical cart; and the medical cart includes the radiation generation apparatus and the hardware processor.

3. The mobile radiographic imaging system according to claim 2, wherein:

the hardware processor is at least one of (1) a hardware processor that controls the medical cart, and (2) a hardware processor that controls a building in which the management area is installed; and the hardware processor executes at least one of (1) outputting a warning to a user, and (2) causing the medical cart to restrict emission of the radiation outside the management area.

4. The mobile radiographic imaging system according to claim 3, wherein:

the warning is output in at least one of cases below:

(1) before movement of the medical cart and/or at a start of the movement, (2) when a fixer of the medical cart is released, (3) when the medical cart is disconnected from a commercial power supply, (4) when the medical cart acquires imaging information from a radiology information system (RIS), (5) when communication between a main body of the medical cart and the radiation detection apparatus is switched from wired communication to wireless communication, (6) when it is detected that a handle of the medical cart is held, (7) when the movement of the medical cart is detected, (8) during the movement of the medical cart, (9) when the medical cart has moved a predetermined distance,

(10) when a predetermined time has elapsed since the start of the movement of the medical cart,

(11) after the medical cart moves,

(12) when the fixer of the medical cart is locked,

(13) when the medical cart is connected to the commercial power supply, and

(14) when a start of imaging is instructed.

5. The mobile radiographic imaging system according to claim 3, wherein the warning is a notification by at least one of (1) displaying on a monitor, (2) turning on a light, and (3) outputting sound.

6. The mobile radiographic imaging system according to claim 3, wherein the warning provides a notification of at least one of (1) a current mode being a fluoroscopy mode, (2) the current mode, and (3) mode setting having been completed.

7. The mobile radiographic imaging system according to claim 2, wherein the hardware processor is a hardware processor that controls the medical cart, and executes at least one of (1) outputting a warning to a user, and (2) causing the radiation generation apparatus to restrict emission of the radiation outside the management area.

8. The mobile radiographic imaging system according to claim 7, wherein when the radiation generation apparatus is set to the first mode, the hardware processor prevents the medical cart from moving outside the management area.

9. The mobile radiographic imaging system according to claim 8, wherein the hardware processor executes at least one of (1) controlling a fixer configured to fix the medical cart, and (2) fixing the medical cart to a wire fixed to a wall forming the management area.

10. The mobile radiographic imaging system according to claim 7, wherein when the radiation generation apparatus is located outside the management area, the hardware processor executes control to prohibit the radiation generation apparatus from emitting the radiation at a radiation dose exceeding an allowable radiation dose.

11. The mobile radiographic imaging system according to claim 10, wherein when the hardware processor recognizes that the radiation generation apparatus is set to the first mode and the medical cart is located outside the management area, the hardware processor executes at least one of (1) shutting down the medical cart, (2) stopping power supply to the medical cart, (3) cutting off the power supply to the radiation generation apparatus, (4) switching a mode of the radiation generation apparatus to the second mode, (5) disabling the first mode, (6) preventing emission of the radiation exceeding the allowable radiation dose from the radiation generation apparatus, and (7) preventing setting of a fluoroscopy mode.

12. The mobile radiographic imaging system according to claim 2, wherein the hardware processor is a hardware processor that controls a building in which the management area is installed, and executes at least one of (1) outputting a warning to a user, and (2) causing the radiation generation apparatus to restrict emission of the radiation outside the management area.

13. The mobile radiographic imaging system according to claim 12, wherein when the medical cart is located inside the management area, the hardware processor executes at least one of (1) locking a key of a door forming the management area, and (2) fixing a wire fixed to the medical cart to a wall forming the management area.

14. A method of restricting a mobile radiographic imaging system, wherein in the mobile radiographic imaging system that is configured to be set to a plurality of imaging modes including a first mode for performing fluoroscopic imaging and a second mode that is a general imaging mode and wherein a series of frame images is acquired by irradiating a subject with the radiation in the second mode, use of the first mode is restricted outside a management area.

* * * * *